Sept. 4, 1956 R. E. SHEPHERD Plant Pat. 1,511
ROSE PLANT
Filed Oct. 25, 1955
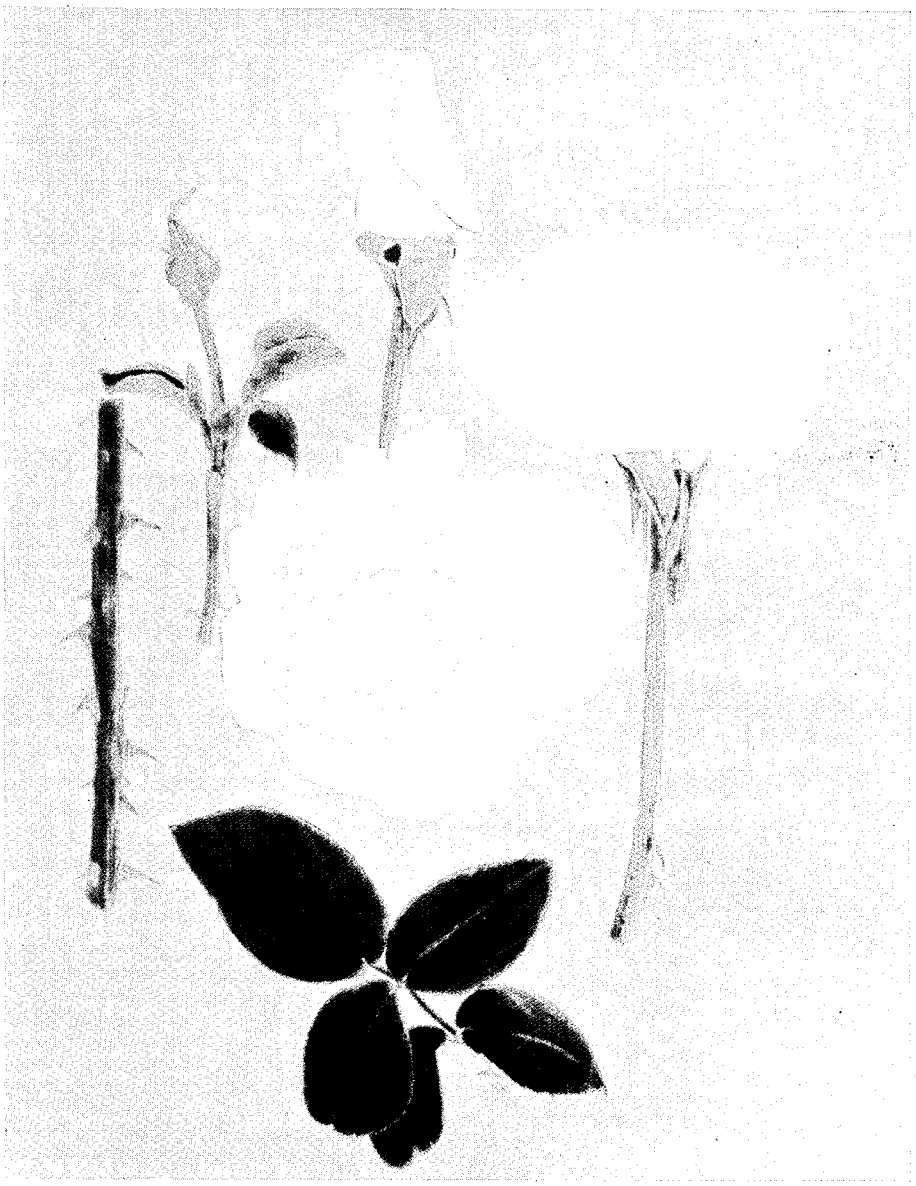
INVENTOR
Roy E. Shepherd
By Orville M. Kile
Plant Patent Agent.

United States Patent Office

Plant Pat. 1,511
Patented Sept. 4, 1956

1,511

ROSE PLANT

Roy E. Shepherd, Medina, Ohio, assignor to Edith C. Bosley, Mentor, Ohio

Application October 25, 1955, Serial No. 542,797

1 Claim. (Cl. 47—61)

My present invention is an improvement in hybrid tea rose plants and relates to a new and improved variety obtained by crossing the varieties Mme. Henri Guillot (Plant Patent No. 337) and Peace (Plant No. 591), the cross having been made by me at my greenhouse at Medina.

I have asexually reproduced the variety at the same location by means of budding, and its characteristics appear to be permanent.

The accompanying illustration shows in full colors, a tight bud, an opening bud, two open flowers in different positions, and separated portions of stem and foliage.

In the following detailed description of the plant and flower, color plate numbers refer to Ridgway's Color Standards and Nomenclature, while in other references to color the ordinary dictionary meaning is intended.

THE PLANT

Growth habit: Exceedingly vigorous upright bush; very free-branching.

Canes: Heavy.

Stems:

*Strength.*—Stout and strong.

*Length.*—Medium to long.

*Internodes.*—Rather short.

*Color.*—Approximately Elm Green (Pl. XIII), tinged with Pompeian Red (Pl. XIII).

*Thorns.*—Large; sharp; downward-pointing; numerous: red-tinged; and irregularly spaced.

Foliage:

*Leaves.*—Pinnately compound, usually with five leaflets.

*Quantity.*—Plentiful.

*Color.*—Approximately Dark Dull Yellow-Green (Pl. XXXII) on the upper surface and Bice Green (Pl. XVII) on the under surface. New foliage is slightly red-tinged.

*Rachis.*—Slender; deeply grooved and smooth above; medium heavy; has occasional thorn on under side.

*Stipules.*—Narrow; short points.

*Disease resistance.*—Particularly resistant to diseases, especially blackspot. Under ordinary garden conditions, it is practically impossible to produce blackspot on its foliage.

THE BLOOM

Bud:

*Size.*—Medium to large.

*Form.*—Conical-pointed, with wide base.

*Color.*—Tight bud is Cedar Green (Pl. VI). As first petal breaks, inside of petals is Rose Red (Pl. XII) combined with Rose Doree (Pl. I) with an aiglet of Lemon Chrome (Pl. IV). Outside is Geranium Pink (Pl. I), also with the Lemon Chrome aiglet.

*Peduncle.*—Medium length; strong, stiff and erect. Approximately same color as stems.

*Sepals.*—Simple; only slightly foliaceous; hood over tight bud; reflex early.

Flower:

*Borne.*—Singly, on long stems.

*Size.*—Large. 4 to 5 inches across.

*Form.*—High-centered, becoming cup-shaped and revealing stamens only in late stages of opening of some of the flowers. Central petals curve inward to make the covered center, while the remaining petals spread loosely.

*Color.*—In the opening rose the inner surface is Rose Doree (Pl. I), blended with some Spectrum Red (Pl. I), and some Rose Red (Pl. XII), with edges of Begonia Rose (Pl. I) and an aiglet of Lemon Chrome (Pl. IV). The under surface is Geranium Pink, blended with some Shrimp Pink (Pl. I). The open flower shows its outer petals to be Rose Red blended with Rose Color (Pl. XII) and its intermediate petals Rose Red (Pl. XII) blended with Scarlet Red (Pl. I). The center petals are Rose Doree blended with Scarlet Red (Pl. I) on their supper surface, but Strawberry Pink (Pl. I) on the under surface which is the part usually visible at this stage because of the inward turning of these petals.

It will be noted that the colors are similar but somewhat lighter than those of this variety's parent, Mme. Henri Guillot, the variety which it most resembles.

*Petalage.*—Double, with an average of from 25 to 30 petals in mid-October in northern Ohio.

*Behavior.*—Drop off cleanly, without fading.

*Longevity.*—Exceptionally good both on bush and as cut flowers.

Petals:

*Shape.*—Approximately round. Edge sometimes slightly wavy and slightly rolled. Entire except for a notch frequently found at tip.

*Substance.*—Substantial.

Reproductive organs:

*Pistils.*—Many; very tightly bunched and sitting atop a pithy mound.

*Stamens.*—Many, surrounding pithy mound. Filaments curved inward from edge of mound or ring. Anthers large; bright yellow.

Having thus disclosed my invention, I claim:

The new and distinct variety of hybrid tea rose plant, substantially as herein shown and described, characterized particularly by its exceptionally vigorous growing habit, its healthy foliage especially resistant to blackspot; and its large, well-formed blooms of distinctive coloring of blends of Rose Doree to Rose Red on the inner surface of their petals and much lighter tones of the same coloring on the outer surface.

No references cited.